United States Patent [19]

DiMarchi et al.

[11] Patent Number: 4,782,139
[45] Date of Patent: Nov. 1, 1988

[54] SELECTIVE CHEMICAL REMOVAL OF A PROTEIN AMINO-TERMINAL RESIDUE

[75] Inventors: Richard D. DiMarchi, Carmel; Gerald S. Brooke, Indianapolis, both of Ind.

[73] Assignee: Eli Lilly and Company, Indianapolis, Ind.

[21] Appl. No.: 922,436

[22] Filed: Oct. 23, 1986

Related U.S. Application Data

[63] Continuation-in-part of Ser. No. 791,837, Oct. 28, 1985, abandoned.

[51] Int. Cl.$^4$ .................... A61K 37/24; C07C 103/52; C07G 7/00
[52] U.S. Cl. ............................ 530/407; 530/303; 530/350; 530/351; 530/380; 530/399; 514/2; 514/3; 514/12; 514/21
[58] Field of Search ............... 530/407, 303, 350, 351, 530/380, 399; 424/177

[56] References Cited

U.S. PATENT DOCUMENTS 4,426,378 1/1984 Holaday .................... 514/18

OTHER PUBLICATIONS

Mazur, R. H., and Schlatter, J. M., *J. Org. Chem.*, 28, 1025–1029 (1963).
Gisin, B. F., and Merrifield, R. B., *J. Amer. Chem. Soc.*, 94, 3102–3106 (1972).

*Primary Examiner*—Morton Foelak
*Assistant Examiner*—Nathan M. Nutter
*Attorney, Agent, or Firm*—William C. Martens; Leroy Whitaker

[57] ABSTRACT

The invention relates to a process and compounds useful therein for producing a compound having an amino acid sequence defining a biologically active peptide or protein from a compound of the formula

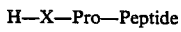

H—X—Pro—Peptide in which X is the residue of a naturally occurring amino acid and Peptide is a sequence of amino acids defining a biologically active peptide or protein, which comprises subjecting H—X—Pro—Peptide to conditions under which a diketopiperazine of the H—X—Pro— moiety is formed with accompanying cleavage and release of Peptide.

30 Claims, No Drawings

SELECTIVE CHEMICAL REMOVAL OF A PROTEIN AMINO-TERMINAL RESIDUE

CROSS-REFERENCE

This application is a continuation-in-part of Application Ser. No. 791,837 filed Oct. 28, 1985, and now abandoned.

BACKGROUND OF THE INVENTION

The biosynthesis of proteins in genetically altered procaryotic cells results in expression of a protein having an N-formyl-methionine attached at the amino terminus. Since the addition of N-formylmethionine to the native protein may alter its biological activity, conformational stability, antigenicity, etc., it is most desirable, if possible, to remove it.

By insertion of a cleavage site between the amino-terminal methionine and the desired native peptide, one in theory has a greater degree of flexibility in the methodology selected for achieving production of the desired native peptide. In fact, however, there are only a very limited number of practical methods for achieving selective cleavage.

For example, in those native proteins in which methionine is not present, cyanogen bromide mediated cleavage (methionine being the selective cleavage site) has proven to be a very effective method for generating native protein. In fact, however, the absence of methionine is a rare occurrence in moderately-sized peptides and proteins. Consequently, a most important objectie is to discover a method by which the aminoterminal methionine can be cleaved with generation of the native biosynthetically-produced protein.

A key and unexpected observation determining any approach for generating native protein from amino terminal methionyl protein is that the α-amino group of the biosynthetic expression product, for example, $N^\alpha$-methionyl-(human growth hormone), is not formylated. This fact was first observed through chemical modification of the expression product with cyanate and later was confirmed by automated Edman sequence analysis. The E. coli expression organism, although incapable of cleavage of the initiating methionine, nevertheless, did effect removal of the $N^\alpha$-formyl group, presumably enzymatically. Consequently, the α-amino group of the amino-terminal methionine expression product is directly available (potentially at least) for cleavage.

Having a free α-amino group on the amino-terminal methionyl expression product gives rise to the possibility of other approaches for methionyl removal. One approach, a selective Edman-type amino terminal sequential cleavage using phenyl isothiocyanate, for practical application requires the absence of lysine residues in the native protein. However, only the rarest of proteins will be free of lysine.

Another possible approach is the use of an exopeptidase; in principle, these will achieve stepwise amino acid scission. Reports of successful utilization of exopeptidases in synthetic studies have been quite scarce for a number of reasons, including their heterogeneous nature, expense, susceptibility to denaturation, and, most importantly, their wide variability in specific and non-specific action against differing substrates.

A new methodology has been discovered which represents novel chemical procedures and provides new compounds useful in achieving selective amino-terminal cleavage to produce the desired end peptide product. It is to such a process and to compounds useful therein that this invention is directed.

SUMMARY OF THE INVENTION

Thus, this invention relates to a class of compounds having the formula

in which X is the residue of a naturally occurring amino acid; and Peptide is a sequence of amino acid residues defining that of a biologically active peptide or protein.

This invention also is directed to a process for producing a compound having an amino acid sequence representing that of a biologically active peptide or protein from a compound of the formula

in which X is the residue of a naturally occurring amino acid and Peptide is a sequence of amino acids representing that of a biologically active peptide or protein. In one embodiment, the process comprises subjecting H—X—Pro—Peptide to weakly acid conditions in an aprotic solvent. In a second embodiment of the process H—X—Pro-Peptide is subjected to acid, neutral, or alkaline conditions in a buffered aqueous medium. In either embodiment a diketopiperazine of the H—X—Promoiety is formed with accompanying cleavage and release of Peptide.

DETAILED DESCRIPTION OF THE INVENTION

The methodology that has been discovered and which represents the substance of this invention involves the designed biosynthetic production of a compound of the formula

in which X and Peptide have the meanings as hereinbefore defined. The compound can be produced using now routine recombinant DNA techniques and can be obtained either as a direct expression product or indirectly as a result of treatment of a precursor expression product.

The compound H—X—Pro—Peptide is extremely useful for obtaining the desired compound designated by the term "Peptide", which compound could not have been prepared directly via recombinant DNA methodology. The compound H—X—Pro—Peptide, when treated in accordance with the process of this invention, results in formation of the desired product (Peptide) via intermediate diketopiperazine formation. The acid cleavage is generally depicted in the following sequence:

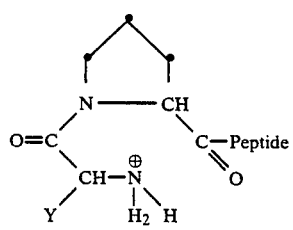

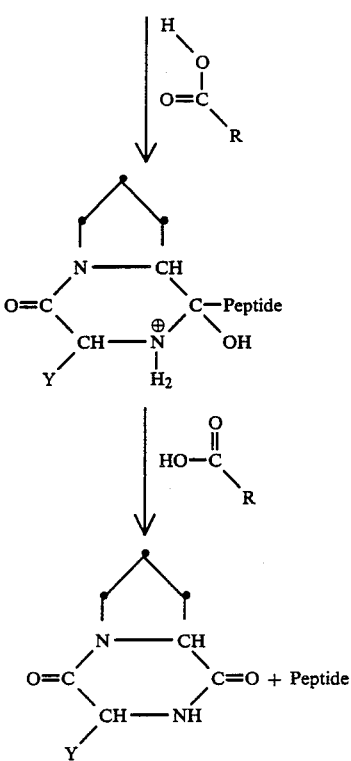

the foregoing, the group Y is the side chain of a naturally occurring amino acid.

The group X in the compounds of this invention denotes a residue of any of the naturally occurring amino acids. Preferably, however, the amino acid residue represented by X is other than proline since a Pro-Pro sequence will only very slowly form the desired diketopiperazine intermediate through which the cleavage will proceed. Most often, the compounds of this invention will be produced via recombinant DNA methodology. When the compound of this invention is produced directly as the expression product, the group X will be methionyl; X, therefore, in the context of this invention, most preferably is methionyl. However, when the group X is other than methionyl, the source of the compound again may be biosynthetic. The expression product, however, will have first been treated by any of a number of methods to produce H—X—Pro—Peptide.

The term "Pro" as used herein refers to the amino acid residue of the naturally occurring amino acid proline.

The group designated "Peptide" refers to a sequence of amino acid residues representing that of any of a wide range of biologically active peptides and proteins including, for example, proinsulin, human growth hormone, bovine growth hormone, α-interferon, β-interferon, γ-interferon, interleukin-1, interleukin-2, growth hormone release factor, insulin-like growth factors, tissue plasminogen activator, protein C, and the like, as well as appropriately modified forms of recognized biologically active peptides and proteins.

Examples of H—X—Pro—Peptide are:
Met-Pro-(human growth hormone);
Ala-Pro-(α-interferon);
Met-Pro-(interleukin-2);
Met-Pro-(γ-interferon);
Met-Pro-(bovine growth hormone);
Met-Pro-(tissue plasminogen activator);
Ser-Pro-(human growth hormone);
Asp-Pro-(human growth hormone);
Met-Pro-(growth hormone release factor);
Met-Pro-(protein C);
Leu-Pro-(insulin-like growth factor);
and the like.

The compounds of this invention, structured such that two specifically defined amino acid residues have been added to the desired end product peptide, afford generation of a wide range of otherwise unavailable biologically active polypeptides and proteins. The compounds, having at their amino terminus a dipeptide composed of a natural amino acid residue followed in sequence by a proline residue, are tailored to permit ready cleavage of the dipeptide and generation of the desired end product. The penultimate proline exerts a cis-conformation on the amino terminal dipeptide and thereby fixes the terminal α-amino in a more favored location for attack at the proline carbonyl [see Gisin, B. F., and Merrifield, R. B., J. Am. Chem. Soc. 94, 3102–3106 (1972)]. Nucleophilic attack at this site is favored by formation of the energetically favored cyclic amino acid-proline diketopiperazine with release of the desired peptide as the leaving group. An essential feature of the reaction in an aprotic solvent is its catalysis by weak acid. A question, key to the feasibility of that embodiment of the process of this invention and the answer to which could not be predicted, is whether the amino-terminal residue of the desired end product could and would serve as a suitable leaving group so as to depart with diketopiperazine formation under conditions in which the desired end product would be both stable and soluble. It appears, although the volume of published solid phase peptide synthesis literature is vast, that diketopiperazine formation has only been reported at the dipeptidyl stage of synthesis where hydrolysis is of the functionalized resin ester linkage. The absence of any reports of diketopiperazine formation at X-Pro sequences where amide hydrolysis is required is not surprising due to the generally accepted principle of increased acid stability of amides when compared to esters. This silence argues strongly against the potential success of the process of this invention.

The treatment of the H—X—Pro—Peptide compound in accordance with the first embodiment of the process of this invention is carried out in an aprotic solvent, preferably substantially free of water. In general, that condition can be met merely by avoiding any affirmative addition of water. Examples of aprotic solvents are 1-methylpyrrolidinone (NMP), N,N-dimethylformamide (DMF), dimethyl sulfoxide (DMSO), formamide, hexamethylphosphoramide (HMPA), and the like. Preferred solvents are NMP, DMF, and DMSO, and, of these, NMP is most preferred. The reaction when conducted in the aprotic solvent is conducted under weakly acidic conditions using acetic acid, phosphoric acid, phosphorous acid, sulfuric acid, trifluoroacetic acid, formic acid, maleic acid, tartaric acid, glycine, and the like. A highly preferred acid is acetic acid.

The cleavage reaction also can be conducted in an aqueous medium. When water is the reaction medium, it is preferred to conduct the reaction in a phosphate buffer.

When conducted in an aprotic solvent, the process of this invention generally will be carried out at a temperature within the range of from about 15° C. to about 50° C., preferably from about 25° C. to about 40° C. The acid concentration usually will range from about 0.1M to about 1M, preferably from about 0.25M to about 0.5M, most preferably from about 0.30M to about 0.35M, and specifically about 0.33M.

When conducted in an aqueous medium, both the temperature and acid concentration preferably will be somewhat higher. Thus, for example, the temperature generally will range from about 25° C. to about 60° C., preferably from about 35° C. to about 50° C. The choice of reaction temperature is dependent on the stability of "Peptide" and the nature of the third amino acid in H—X—Pro—Peptide. As high a temperature as possible, consistent with stability and the nature of the third amino acid residue, is preferred. The buffer concentration usually will range from about 0.1M to about 2M, preferably from about 0.5M to about 1M, and most preferably from about 0.8M to about 1M. The preferred buffering salt is phosphate. A pH of about 8 is preferred as the yield of cleavage is only slightly increased at higher pH values and the possibility of undesirable side effects is greater at the higher values [see McKerrow, J. H., and Robinson, A. B., *Analytical Biochem.* 42, 565–568 (1972)].

The cleavage reaction is conducted with periodic monitoring of diketopiperazine formation. The reaction is terminated when deemed appropriate, and the cleavage product is recovered from the reaction mixture using recognized isolation methodology.

The following is provided as examples to illustrate this invention. The examples are not intended to be limiting on the broad scope of the invention.

Selected peptides, useful as models for the present invention, were prepared by solid phase synthetic methodology. Their purity was confirmed by high performance liquid chromatography. Prior to cleavage, the peptides were stored as amorphous lyophilized solids. A number of experimental parameters were varied. Their effect on cleavage is reported herein.

The following describes the optimized conditions using organic and aqueous media, respectively, and applied to the peptide Met—Pro—Gly—Gly—NH$_2$, in which "—NH$_2$" signifies the presence of an amide moiety at the C-terminus of the peptide.

A. Organic Cleavage Conditions

Ten milligrams of Met—Pro—Gly—Gly—NH$_2$ were dissolved in 1 ml of N-methylpyrrolidinone which had been made anhydrous by storage over 4Å. A molecular sieves for one week. The mixture was maintained at 25° C. with constant stirring, and the reaction was initiated by addition of glacial acetic acid (HOAc) to a concentration of 0.33M. The rate of cleavage was monitored by appearance of methionyl-proline diketopiperazine formation and disappearance of starting peptide as measured in reverse phase chromatographic analysis. Chromatography was achieved using a 0.46×25 cm column of Ultrosphere C$_{18}$ in 0.1% trifluoroacetic acid (TFA), using an acetonitrile gradient to effect elution. The reaction was stopped at each analysis time point by ten-fold dilution with 0.1% trifluoroacetic acid. The diketopiperazine peak was collected and its identity confirmed by amino acid and mass spectral analysis.

Analysis of the products obtained via the foregoing cleavage methods upon a representative sampling of peptides and proteins was assessed by high performance anion exchange and reverse phase chromatography. Anion exchange chromatography was conducted on a Mono Q column in a 0.05M Tris, pH 8.0 buffer containing 30% acetonitrile. Elution was provided using a linear gradient of sodium chloride. Reverse phase analysis was performed on a Zorbax C$_8$, 150Å pore size column using an acetonitrile gradient in 0.1M ammonium phosphate at 45° C., pH 7.0.

The following Tables 1–8 provide results obtained using organic cleavage conditions but varying selected parameters.

Table 1 reports the level of diketopiperazine formation at varying acid concentrations when the cleavage is carried out at 25° C. in DMF. An appreciable rate of reaction is recorded, and it is observed to be dependent upon weak acid concentration. Similar weak acid treatment in DMSO revealed a reduced rate of cleavage. Increasing the temperature of cleavage to 40° C. in DMSO revealed comparable rates of reaction to those achieved in DMF at 25° C., as shown in Table 2.

TABLE 1

Acid Concentration
(Methionine-Proline Diketopiperazine Formation
from Met—Pro—Gly—Gly—NH$_2$ at 25° C.)

| Reagent | Reaction Time, Hours | | |
|---|---|---|---|
| | 2 | 4 | 6 |
| 10 M HOAc/DMF | 2% | 8% | 40% |
| 1 M HOAc/DMF | 26% | 44% | 55% |
| 0.1 M HOAc/DMF | 13% | 28% | 34% |
| 0.01 M HOAc/DMF | 3% | 6% | 8% |
| 100% DMF | 0% | 3% | 4% |
| 100% HOAc | <1% | <1% | 2% |
| 100% TFA | 0% | <1% | <1% |

TABLE 2

Acid Concentration
(Methionine-Proline Diketopiperazine Formation
from Met—Pro—Gly—Gly—NH$_2$ at 40° C.)

| Reagent | Reaction Time, Hours | | |
|---|---|---|---|
| | 2 | 4 | 24 |
| 0.1 M HOAc/DMSO | 25% | 45% | 95% |
| 0.33 M HOAc/DMSO | 38% | 61% | 100% |
| 1.0 M HOAc/DMSO | 27% | 44% | 94% |
| 3.3 M HOAc/DMSO | 7% | 12% | 41% |
| 10.0 M HOAc/DMSO | 2% | 4% | 14% |

As the foregoing demonstrates, the apparent optimal acid concentration is about 0.25M to about 0.5M.

Table 3 provides results studying the effect of temperature on a series of peptides in which only the side chain of the third residue is varied. It is quite clear that increased steric hindrance at this site will slow the rate of reaction. However, in all cases, appreciable cleavage was noted.

TABLE 3

Temperature Effect
(Methionine-Proline Diketopiperazine Formation
in 1M Acetic Acid/DMF at Two Temperatures)

| Peptide[b] | Reaction Time at 25° C., Hours | | Reaction Time at 40° C., Hours | |
|---|---|---|---|---|
| | 2 | 24 | 2 | 24 |
| MPGG—NH$_2$ | 27% | 100% | 76% | 100% |
| MPTG—NH$_2$ | N.D.[a] | N.D. | 22% | 88% |
| MPPG—NH$_2$ | N.D. | N.D. | 20% | 95% |

TABLE 3-continued

Temperature Effect
(Methionine-Proline Diketopiperazine Formation
in 1M Acetic Acid/DMF at Two Temperatures)

| Peptide[b] | Reaction Time at 25° C., Hours | | Reaction Time at 40° C., Hours | |
|---|---|---|---|---|
| | 2 | 24 | 2 | 24 |
| MPFG—NH$_2$ | 2% | 17% | 10% | 68% |

[a]N.D., Not Determined
[b]MPGG—NH$_2$ = Met—Pro—Gly—Gly—NH$_2$
MPTG—NH$_2$ = Met—Pro—Thr—Gly—NH$_2$
MPPG—NH$_2$ = Met—Pro—Pro—Gly—NH$_2$
MPFG—NH$_2$ = Met—Pro—Phe—Gly—NH$_2$ An important factor is the choice of the aprotic solvent. The solvent must be one which promotes or at least does not inhibit diketopiperazine formation with accompanying cleavage to produce the desired end product while at the same time having minimal degradative effect on the ultimate peptide product. Tables 4–8 provide results from studies designed to elicit information as to the properties of a variety of solvents for use under organic cleavage conditions.

Table 4 provides stability information of a number of proteins and peptides when subjected to organic cleavage conditions. The amount in percent, as determined by reverse phase high performance liquid chromatography (HPLC), remaining after subjecting the selected protein or peptide to the defined reaction medium for the stated time in hours is provided and shows, as between DMF and DMSO, the relative superiority of DMSO.

TABLE 4

| | Protein Stability | | | | | |
|---|---|---|---|---|---|---|
| | 1M HOAc/DMF, 40° C. | | | 1M HOAc/DMSO, 40° C. | | |
| Protein[a] | 2 h | 24 h | 48 h | 2 h | 24 h | 48 h |
| Glucagon | 100%[b] | 49% | 37% | 124% | 117% | 119% |
| bPP | 42% | 40% | 32% | 52% | 90% | 86% |
| GRF | 79% | 26% | 0% | 98% | 89% | 86% |
| A(SO$_3^-$)$_4$ | 100% | 58% | 36% | 100% | 100% | 96% |
| B(SO$_3^-$)$_2$ | 97% | 62% | 37% | 94% | 106% | 68% |
| Proinsulin | 86% | 43% | 30% | 97% | 70% | 86% |

[a]bPP = bovine pancreatic polypeptide
GRF = growth hormone release factor
A(SO$_3^-$)$_4$ = insulin A-chain S-sulfonate
B(SO$_3^-$)$_4$ = insulin B-chain S-sulfonate
[b]The relative percent remaining is determined against an untreated external control.

Table 5, similar to Table 4, provides stability results using methionyl human growth hormone, in which NMP proved to be more nearly like DMSO than DMF.

TABLE 5

Stability of Methionyl Human Growth Hormone

| Reagent | Reaction Time at 40° C., Hours | | |
|---|---|---|---|
| | 2 | 4 | 24 |
| 0.33 M HOAc/DMF | 78[a]/78[b] | 65/68 | 45/34 |
| 0.33 M HOAc/DMSO | 91/100 | 77/99 | 75/86 |
| 0.33 M HOAc/NMP | 85/90 | 70/89 | 77/75 |

[a]Determined by reverse phase HPLC
[b]Determined by anion exchange HPLC

Table 6 elaborates the results studying the effect of a number of solvents on cleavage of Met—Pro—Gly—Gly—NH$_2$.

TABLE 6

Solvent Effect
(Disappearance of Met—Pro—Gly—Gly—NH$_2$ as a
Function of Met—Pro Diketopiperazine Formation)

| Reagent | Reaction Time at 25° C., Hours | | | | |
|---|---|---|---|---|---|
| | 0 | 2 | 4 | 6 | 24 |
| 1 M HOAc/CH$_3$CN | 100%[a] | 114% | 105% | 99% | 66% |
| 1 M HOAc/nPrOH | N.D.[b] | 100% | 97% | 94% | 72% |
| 1 M HOAc/MeOH | 100% | 101% | 99% | 99% | 97% |
| 1 M HOAc/CH$_2$Cl$_2$ | 100% | 104% | 96% | 99% | 80% |
| 1 M HOAc/DMF | 100% | 88% | 71% | 57% | 11% |
| 1 M HOAc/DMSO[c] | 100% | 73% | 56% | N.D.[a] | 6% |

[a]Represents the quantity of starting material remaining.
[b]N.D., Not Determined
[c]Determined at 40° C.

From the foregoing, the highly preferred solvents are NMP, DMF, and DMSO, all aprotic organic solvents.

Table 7 provides results studying the effect of temperature on a variety of peptides using DMF or DMSO as solvent.

TABLE 7

Temperature Effect
(Methionine-Proline Diketopiperazine Formation
in two selected solvents at 1M HOAc, 40° C.)

| Peptide[a] | DMF (Time in Hours) | | DMSO (Time in Hours) | | |
|---|---|---|---|---|---|
| | 2 | 24 | 2 | 24 | 48 |
| MPGG—NH$_2$ | 76% | 100% | 36% | 100% | 100% |
| MPTG—NH$_2$ | 22% | 88% | 3% | 11% | 38% |
| MPPG—NH$_2$ | 20% | 95% | 5% | 43% | 65% |
| MPFG—NH$_2$ | 10% | 68% | 1% | 12% | 23% |

[a]MPGG—NH$_2$ = Met—Pro—Gly—Gly—NH$_2$
MPTG—NH$_2$ = Met—Pro—Thr—Gly—NH$_2$
MPPG—NH$_2$ = Met—Pro—Pro—Gly—NH$_2$
MPFG—NH$_2$ = Met—Pro—Phe—Gly—NH$_2$

As the data from Table 7 and the foregoing other tables show, DMF relative to DMSO has a greater effect on diketopiperazine formation and accompanying cleavage; however, it also has a greater degrading effect on product protein or peptide. A fine balance in selection of reaction conditions with respect any particular peptide or protein product must be determined and applied for achieving optimal results.

Table 8 presents data resulting from the application of organic cleavage conditions to a model peptide that mimics a compound of this invention in which the group Peptide is human growth hormone. It is noteworthy that human growth hormone presents a special situation since the first two amino acids of human growth hormone are Phe—Pro. Thus, it is possible to form the diketopiperazine from X—Pro of a compound of this invention and to find a succeeding diketopiperazine form from the initiating Phe—Pro of the resulting human growth hormone. Table 8 thus compares Met—Pro—Phe—Pro—Thr—Ile—NH$_2$ with Phe—Pro—Thr—Ile—NH$_2$. The results show a slower diketopiperazine formation from the latter. Thus, the conditions of treatment of the compound Met—Pro—human growth hormone, a compound of this invention, can be precisely determined so as to maximize the single diketopiperazine formation and accompanying cleavage with minimal secondary diketopiperazine formation. In this regard, NMP is a most desirable solvent since the level of diketopiperazine formation is significantly greater than that in DMSO and almost matches that achieved in DMF, at later time points. When considering the increased stability of growth hormone to NMP than to DMF (Table 5), the former clearly is the desired solvent, at least for this application.

TABLE 8

Diketopiperazine Formation from Growth Hormone Model Peptides

| Reagent | Reaction Time at 40° C., Hours | | | |
|---|---|---|---|---|
| | 2 | 4 | 6 | 24 |
| | Met—Pro—Phe—Pro—Thr—Ile—NH$_2$ | | | |
| 0.33 M HOAc/NMP | 17% | 32% | 47% | 99% |
| 0.33 M HOAc/DMSO | 4% | 6% | 27% | 33% |
| 0.33 M HOAc/DMF | 14% | 47% | 63% | 98% |
| | Phe—Pro—Thr—Ile—NH$_2$ | | | |
| 0.33 M HOAc/NMP | 7% | 12% | 23% | 78% |
| 0.33 M HOAc/DMSO | 4% | 7% | 11% | 27% |
| 0.33 M HOAc/DMF | 15% | 26% | 37% | 88% |

B. Aqueous Cleavage Conditions

Optimal aqueous cleavage of Met—Pro—Gly—Gly—NH$_2$ was achieved by dissolving 1 mg of the peptide in 1M sodium phosphate buffer, pH 8.0. To accelerate the cleavage, the temperature was maintained at 55° C. for 24 hours. The degree of cleavage was determined in the manner described for organic cleavage.

The following Tables 9 to 12 provide results obtained using acid, neutral or alkaline conditions in a buffered aqueous medium.

Table 9 reports the cleavage yield at pH 7.0 using the peptide Met—Pro—Gly—Gly—NH$_2$ as substrate. Three different temperatures were examined with two different buffering salts and concentrations. The results show that phosphate buffer is to be preferred over acetate with a concentration of 1.0M providing the best results.

TABLE 9

Effect of Different Buffer Systems and Concentrations on Methionine-Proline Diketopiperazine Formation from Met—Pro—Gly—Gly—NH$_2$ at pH 7.0

| Buffer | Formation* | | |
|---|---|---|---|
| | 100° C. | 40° C. | 25° C. |
| 0.1 M Sodium Phosphate | 100% | 70% | 14% |
| 1.0 M Sodium Phosphate | 100% | 93% | 25% |
| 0.1 M Sodium Acetate | 55% | 12% | 1% |
| 1.0 M Sodium Acetate | 86% | 35% | 4% |

*Methionine-proline diketopiperazine formation at 100° C. was measured at 2 hours. Formation at 40° C. and 25° C. was measured at 72 hours.

A study of the effect of pH on methioneproline diketopiperazine formation from Met—Pro—Gly—Gly—NH$_2$ at 40° C. in buffered aqueous medium is reported in Table 10. Sodium phosphate was used as the buffer salt. The results show that an alkaline pH is to be preferred. As undesirable side reactions, such as deamidation and desulfurization, are accelerated at elevated pH values, a pH of about 8 is preferred.

TABLE 10

Effect of pH on Methionine-Proline Diketopiperazine Formation in 1.0 M Sodium Phosphate at 40° C.

| | Time in Hours | | | |
|---|---|---|---|---|
| | 4 | 24 | 48 | 72 |
| pH 3 | 1% | 30% | 31% | 9% |
| pH 5 | 2% | 9% | 18% | 25% |
| pH 7 | 18% | 29% | 89% | 92% |
| pH 8 | 27% | 80% | 97% | 100% |

TABLE 10-continued

Effect of pH on Methionine-Proline Diketopiperazine Formation in 1.0 M Sodium Phosphate at 40° C.

| | Time in Hours | | | |
|---|---|---|---|---|
| | 4 | 24 | 48 | 72 |
| pH 9 | 30% | 86% | 98% | 100% |

Table 11 reports the results of an examination of the effect of different buffering salts on the cleavage yield from Met—Pro—Gly—Gly—NH$_2$ at pH 8.0 and 40° C. Sodium phosphate is the preferred buffer.

TABLE 11

Effect of Different Buffering Salts on Methionine-Proline Diketopiperazine Formation from Met—Pro—Gly—Gly—NH$_2$ at pH 8.0 and 40° C.

| Buffer | Time in Hours | |
|---|---|---|
| | 2 | 24 |
| 1.0 M Sodium Phosphate | 22% | 86% |
| 1.0 M Sodium Phosphite | 6% | 40% |
| 1.0 M Sodium Sulfite | 6% | 35% |

Table b 12 reports the results of a study of the effect of temperature on methionine-proline diketopiperazine formation in a series of peptides in which only the side chain of the third residue from the N-terminus is varied. As was the case in the study reported in Table 3, supra, it is clear that increased steric hindrance at the site of the third residue will slow the reaction. However, appreciable cleavage was noted in all but two instances. Increasing the temperature from 40° C. to 55° C. markedly increased the rate and extent of cleavage in all four of the tetrapeptides tested.

TABLE 12

Temperature Effect (Methionine-Proline Diketopiperazine Formation at Two Temperatures in 1.0 M Phosphate Buffer at pH 8.0

| Peptide$^a$ | Reaction Time at 40° C., Hours | | | Reaction Time at 55° C., Hours | | |
|---|---|---|---|---|---|---|
| | 2 | 24 | 48 | 2 | 24 | 48 |
| MPGG—NH$_2$ | 16% | 84% | 96% | 47% | 100% | 100% |
| MPTG—NH$_2$ | 2% | 18% | 26% | 8% | 47% | 75% |
| MPPG—NH$_2$ | 0% | 12% | 19% | 6% | 30% | 53% |
| MPFG—NH$_2$ | 0% | 9% | 14% | 4% | 28% | 57% |

$^a$MPPG—NH$_2$ = Met—Pro—Gly—Gly—NH$_2$
MPTG—NH$_2$ = Met—Pro—Thr—Gly—NH$_2$
MPPG—NH$_2$ = Met—Pro—Pro—Gly—NH$_2$
MPFG—NH$_2$ = Met—Pro—Phe—Gly—NH$_2$

We claim:

1. A compound having the formula

H—X—Pro—Peptide in which X is the residue of a naturally occurring amino acid; and Peptide is a sequence of amino acid residues defining that of a biologically active peptide or protein.

2. Compound of claim 1 in which X is Met.

3. Compound of claim 1 in which Peptide is a sequence of amino acid residues defining proinsulin, human growth hormone, bovine growth hormone, α-interferon, β-interferon, γ-interferon, interleukin-1, interleukin-2, growth hormone release factor, insulin-iike growth factors, tissue plasminogen activator, protein C, or modified, biologically active forms of any of the foregoing.

4. Compound of claim 3 in which Peptide human growth hormone.

5. Compound of claim 3 in which Peptide is bovine growth hormone.

6. A process for producing a compound having an amino acid sequence defining a biological active peptide or protein from a compound of the formula

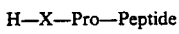

wherein X is the residue of a naturally occurring amino acid and Peptide is a sequence of amino acids defining that of a biologically active peptide or protein, which comprises subjecting H—X—Pro—Peptide to
 (a) weakly acid conditions in an aprotic solvent, or
 (b) acid, neutral or alkaline conditions in a buffered aqueous medium,
under which a diketopiperazine of the H—X—Pro moiety is formed with accompanying cleavage and release of Peptide.

7. Process of claim 6, in which the reaction is carried out in the presence of an aprotic solvent.

8. Process of claim 7, in which the aprotic solvent is selected from the group consisting of N-methylpyrrolidinone, N,N-dimethylformamide, dimethyl sulfoxide, formamide, and hexamethylphosphoramide.

9. Process of claim 8, in which the aprotic solvent is selected from the group consisting of N-methylpyrrolidinone, N,N-dimethylformamide, and dimethyl sulfoxide.

10. Process of claim 9, in which the aprotic solvent is N-methylpyrrolidinone.

11. Process of claim 7, in which the weakly acid conditions are generated by addition of an acid selected from the group consisting of acetic acid, phosphoric acid, phosphorous acid, sulfuric acid, trifluoroacetic acid, formic acid, maleic acid, tartaric acid, and glycine.

12. Process of claim 11, in which the acid is acetic acid.

13. Process of claim 7, in which the reaction is carried out at a temperature of from about 15° C. to about 50° C.

14. Process of claim 13, in which the reaction is carried out at a temperature of from about 25° C. to about 40° C.

15. Process of claim 11, in which the acid concentration is from about 0.1M to about 1M.

16. Process of claim 15, in which the acid concentration is from about 0.25M to about 0.5M.

17. Process of claim 16, in which the acid concentration is from about 0.30M to about 0.35M.

18. Process of claim 10, in which the reaction is carried out using acetic acid at a concentration of about 0.33M.

19. Process of claim 6, in which H—X—Pro—Peptide is subjected to neutral or alkaline conditions in a buffered aqueous medium.

20. Process of claim 19, in which the buffering salt is a phosphate, phosphite, or sulfite salt.

21. Process of claim 20, in which the buffering salt is a phosphate salt present in a concentration of from about 0.1M to about 2.0M.

22. Process of claim 21, in which the phosphate salt is present in a concentration of about 0.8M to about 1.0M.

23. Process of claim 19, in which the reaction is carried out at a pH of from about 7 to about 9.

24. Process of claim 23, in which the reaction is carried out at about pH 8.

25. Process of claim 21, in which the reaction is carried out at a temperature of from about 25° C. to about 60° C.

26. Process of claim 25, in which the reaction is carried out at a temperature of from about 35° C. to about 50° C.

27. Process of claim 6, in which X is Met.

28. Process of claim 27, in which Peptide is a sequence of amino acid residues defining a peptide selected from the group consisting of proinsulin, human growth hormone, bovine growth hormone, α-interferon, β-interferon, γ-interferon, interleukin-1, interleukin-2, growth hormone release factor, insulin-like growth factors, tissue plasminogen activator, protein C, and modified, biologically active forms of any of the foregoing.

29. Process of claim 28, in which Peptide is human growth hormone.

30. Process of claim 28, in which Peptide is bovine growth hormone.

* * * * *